(12) United States Patent
Freixedas et al.

(10) Patent No.: US 8,377,909 B2
(45) Date of Patent: Feb. 19, 2013

(54) USE OF PHYTATE AS AGENT INHIBITING DISSOLUTION OF CRYSTALS OF CALCIUM SALTS FOR THE PREVENTION OF OSTEOPOROSIS

(75) Inventors: Felix Grases Freixedas, Palma de Mallorca (ES); Pilar Sanchis Cortes, Palma de Mallorca (ES); Antonia Costa-Bauza, Palma de Mallorca (ES); Joan Perello Bestard, Palma de Mallorca (ES); Rafael Mara Prieto Almirall, Palma de Mallorca (ES); Bernat Isern Amengual, Palma de Mallorca (ES); Ramon Garcia Gonzalez, Palma de Mallorca (ES)

(73) Assignee: Universitat de les Illes Balears, Palma de Mallorca (ES)

( * ) Notice: Subject to any disclaimer, the term of this patent is extended or adjusted under 35 U.S.C. 154(b) by 512 days.

(21) Appl. No.: 12/302,964

(22) PCT Filed: May 30, 2007

(86) PCT No.: PCT/ES2007/070102
§ 371 (c)(1),
(2), (4) Date: Jan. 29, 2009

(87) PCT Pub. No.: WO2007/138147
PCT Pub. Date: Dec. 6, 2007

(65) Prior Publication Data
US 2009/0203650 A1    Aug. 13, 2009

(30) Foreign Application Priority Data

Jun. 1, 2006   (ES) .................................. 200601519

(51) Int. Cl.
*A61K 31/6615*   (2006.01)
*A61P 19/10*   (2006.01)
(52) U.S. Cl. ..................................................... 514/102
(58) Field of Classification Search .................... 514/102
See application file for complete search history.

(56) References Cited

U.S. PATENT DOCUMENTS

| 5,015,634 | A | 5/1991 | Siren et al. |
| 5,057,507 | A | 10/1991 | Siren et al. |
| 2007/0212449 | A1 | 9/2007 | Shamsuddin et al. |

FOREIGN PATENT DOCUMENTS

| CN | 1295862 | 5/2001 |
| EP | 1 203 535 A1 | 5/2002 |
| WO | WO-9109601 | 7/1991 |
| WO | WO-2004015084 | 2/2004 |
| WO | WO 2005/044278 | * 5/2005 |
| WO | WO 2007/023306 | * 3/2007 |

OTHER PUBLICATIONS

Grases (Study of my-inositol hexaphosphate cream to prevent dystrophic calcinosis cutis, British Journal of Dermatology 2005, 152, pp. 1022-1025).*
Grases (Effects of Phytic Acid on Renal Stone Formation in Rats, Scand Journal Urol Nephrol, Dec. 29, 1997, pp. 261-265).*
Bloom, J.R. and Navon, J.R. "Inhibitory effect of phytate on bone resorption in organ cultures". Journal of dental research, 1979, vol. 58, pp. 156, abstract.
Tripathi et al., "Soybean-a cinsummate functional food: A review" . Journal of Food Sciences and Technology, 2005, vol. 42(2), pp. 111-119, abstract, p. 117, col. 1.
Grases F., Kroupa M. et al, "Studies on calcium oxalate monohydrate crystallisation. Influence of inhibitors". Urol Res 1994; 22: 39-43.
Grases F. Costa-Bauzá A. "Potentiometric study of the nucleation of calcium oxalate in presence of several additives". Clin Chem Enzym Comms 1991; 3: 319-328.
Grases F, Ramis M, Costa-Bauzá A. "Effects of phytate and pyrophosphate on brushite and hydroxyapatite crystallization. Comparison with the action of other polyphosphates". Urol Res 2000; 28: 136-140.
Conte A, Pizá P, et al. "Urinary lithogen risk test: usefulness in the evaluation of renal lithiasis treatment using crystallization inhibitors (citrate and phytate)". Arch Esp Urol 1999; 52: 305-310.
Grases F, Sanchis P. et al., "Phytate (myo-inositol hexakisphosphate) inhibits cardiovascular calcifications in rats". Front Biosci 2006; 11: 136-142.
Gomes, B.C., et al., "Inhibitory effect of inositol phosphates on parathyroid hormone-induced bone resorption in organ cultures," *Journal of Dental Research* 63(6):890-893 (1984).
Kaufman, H.W., "Interactions of inositol phosphates with mineralized tissues," in *Phytic Acid: Chemistry and Applications*, pp. 302-320, Pilatus Press (1986).
Nancollas, G.H., et al. "Novel Insights into actions of bisphosphonates on bone: differences in interactions with hydroxyapatite," *Bone* 38(5) Pergamon Press (May 2006) (Published online Jul. 2005).

* cited by examiner

*Primary Examiner* — Brandon Fetterolf
*Assistant Examiner* — Kathrien Cruz
(74) *Attorney, Agent, or Firm* — Sterne, Kessler, Goldstein & Fox PLLC

(57) ABSTRACT

The present invention relates to the use of myo-inositol hexaphosphate or a pharmaceutically acceptable salt thereof for the manufacture of a medicament for the prevention or treatment of a disease associated with the dissolution of crystals of calcium salts, in particular osteoporosis. These compounds may be utilized in the manufacture of functional foods, dietetic supplements, vitamin supplements, nutritional supplements, food supplements, or phytotherapeutic products having properties of inhibition of dissolution of crystals of calcium salts.

5 Claims, 1 Drawing Sheet

USE OF PHYTATE AS AGENT INHIBITING DISSOLUTION OF CRYSTALS OF CALCIUM SALTS FOR THE PREVENTION OF OSTEOPOROSIS

This application is a U.S. national phase application under 35 U.S.C. §371 of International Patent Application No. PCT/ES2007/070102 filed May 30, 2007, which claims the benefit of priority to Spanish Patent Application No. P200601519 filed Jun. 1, 2006, the disclosures of all of which are hereby incorporated by reference in their entireties. The International Application was published in Spanish on Dec. 6, 2007 as WO 2007/138147.

FIELD OF THE INVENTION

The present invention relates to the use of phytate (myo-inositol hexaphosphate) as an agent inhibiting the dissolution of crystals of calcium salts, particularly calcium phosphate.

In particular, in the medical field, the present invention relates to the use of phytate in the prevention of osteoporosis.

The present invention also relates to various compositions containing phytate for the inhibition of dissolution of crystals of calcium salts.

BACKGROUND

Since the 1960s, when inhibitors of crystallisation were first talked about, many substances were classified as inhibitors due to their ability to prevent or reduce the formation of crystals. However, there is a shortage of substances that prevent the dissolution of already formed crystals, especially in living systems.

The dissolution of already formed salts is especially relevant in some disorders such as osteoporosis. Osteoporosis is a reduction of bone mass and mechanical strength leading to susceptibility to fractures. It is the main cause of bone fractures in post-menopausal women and in old people in general. Osteoporosis does not have a well-defined beginning and until recently, the first visible sign of the disease was often a fracture of the hip, wrist or of vertebrae that gave rise to pain or deformation. Menopause is the main cause of osteoporosis in women due to a reduction in estrogen levels. Osteoporosis affects one out of every five women over age 45 and four out of every ten over age 75.

The best treatment for osteoporosis is prevention. An adequate calcium intake and physical exercise during adolescence and youth can increase the density of bone mass, which results in a reduction in bone mass loss and in less risk of fractures in later years. Adequate consumption of calcium and vitamins during maturity is essential for bone health. Hormone replacement therapy requires strict gynecological control and careful selection of patients. In post-menopausal women with low bone mass or with established osteoporosis and for whom hormone replacement therapy is counterindicated, bisphosphonates (alendronate or etidronate) and calcitonin are effective medicaments for preventing bone loss.

Phytate or myo-inositol hexaphosphate is a molecule whose properties as a crystallisation inhibitor of calcium salts is well known (Grases F, Kroupa M, Costa-Bauzá A. Studies on calcium oxalate monohydrate crystallisation. Influence of inhibitors. Urol Res 1994; 22: 39-43. Grases F. Costa-Bauzá A. Potentiometric study of the nucleation of calcium oxalate in presence of several additives. Clin Chem Enzym Comms 1991; 3: 319-328. Grases F, Ramis M, Costa-Bauzá A. Effects of phytate and pyrophosphate on brushite and hydroxyapatite crystallization. Comparison with the action of other polyphosphates. Urol Res 2000; 28: 136-140). As it is a molecule with six phosphate groups, it shows a high affinity for divalent and trivalent metallic ions, such as calcium. It is precisely this affinity for calcium that leads to its property of inhibition of crystallisation of calcium salts, due to its high ability to adsorb on to surface of nuclei in formation or growing crystals. This ability gives phytate its properties for the prevention of the development of pathological calcifications, such as renal lithiasis (Conte A, Pizá P, García-Raja A, Grases F, Costa Bauzá, Prieto R M. Urinary lithogen risk test: usefulness in the evaluation of renal lithiasis treatment using crystallization inhibitors (citrate and phytate). Arch Esp Urol 1999; 52: 305-310) or cardiovascular calcifications (Grases F, Sanchis P, Perelló J, Isem B, Prieto R M, Fernández-Palomeque C, Fiol M, Bonnin O, Torres J J. Phytate (myo-inositol hexakisphosphate) inhibits cardiovascular calcifications in rats. Front Biosci 2006; 11: 136-142).

Surprisingly, the inventors of the present invention have found that the high adsorption capacity of phytate on calcium salts can be utilised to prevent the dissolution of already precipitated calcium salts, introducing a new property to phytate that has direct repercussions on certain disorders, such as osteoporosis, making it possible to utilise it to treat this disease.

The document that comes closest to the invention in the state of the art is the Chinese patent CN1295862. In summary, the patent discloses a method to treat osteoporosis based on the reaction between egg shell and acetic acid, forming calcium acetate that is used as a calcium supplement for the patient. At the same time, lysozyme and a protein of phytic acid (not phytate directly, but a different compound) were utilised to regulate the absorption of calcium, which is the agent utilised to act against osteoporosis.

In U.S. Pat. Nos. 5,057,507, 5,015,634 and WO9109601, isomers of inositol triphosphate are disclosed for the preparation of medicaments for treatment of bone disorders. As indicated in the description of this invention, the compound of the present invention, due to its structure, presents higher inhibitory potential on crystals of calcium salts and consequently provides more effective medicaments for the treatment of bone disorders, such as osteoporosis.

SUMMARY OF THE INVENTION

The object of the present invention is to find new applications of myoinositol hexaphosphate (also referred to herein as phytate) related with the properties described in the background section.

The objective of the present invention is a composition that includes phytate to prevent the dissolution of crystals of calcium salts.

The applications of phytate described below have not been previously disclosed and their use can be beneficial for the treatment of certain pathologies. In particular, it has been found that the composition including phytate has an inhibitory effect on the dissolution of crystals of calcium salts, such as calcium phosphate, a fact that enables this composition to be utilised in the treatment of osteoporosis.

DETAILED DESCRIPTION OF THE INVENTION

Figure 1:
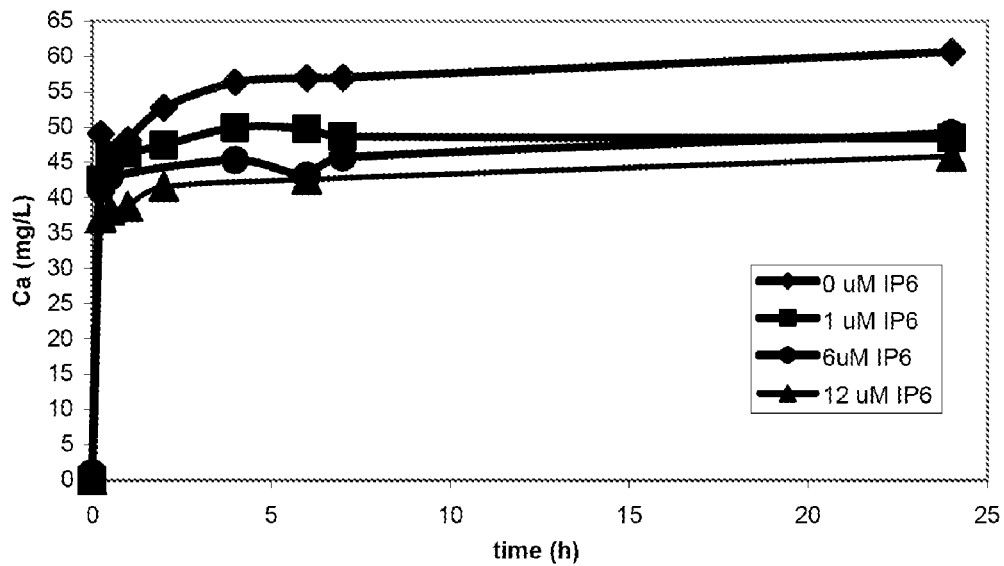
FIG. 1 is a graph showing the quantity of calcium dissolved on treating hydroxyapatite, which has been previously treated with various concentrations of phytate at pH 7.4, for a period of 24 hours.

The present invention relates to the use of phytate (myo-inositol hexaphosphate) or any of the pharmaceutically acceptable salts thereof or mixtures of both for the manufacture of a medicament for the prevention or treatment of diseases associated with the dissolution of crystals of calcium salts, osteoporosis in particular.

The present invention also relates to the use of phytate for the manufacture of an inhibitor of dissolution of crystals of calcium salts, particularly calcium phosphate.

The present invention also relates to the manufacture of a composition, such as a functional food, dietetic supplement, vitamin supplement, nutritional supplement, food supplement or phytotherapeutic product that includes phytate, for avoiding or preventing dissolution of crystals of calcium salts.

In the present invention, it is understood that "phytate" or "myo-inositol hexaphosphate" is the molecule that corresponds to the formula:

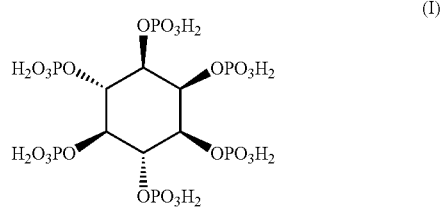

(I)

and its pharmaceutically acceptable salts, which include but are not limited to sodium, potassium, calcium, magnesium, and calcium-magnesium salts, and mixtures thereof.

Phytate is the most naturally abundant inositol phosphate, occurring at high concentrations in cereals, pulses, nuts and seeds in general, in the form of an insoluble salt known as phytine (mixed calcium and magnesium salt). In fact, phytate represents the greatest source of phosphorus for seeds during germination, reaching between 50% and 80% of the total phosphorus. The presence of phytates in biological fluids (blood, urine, saliva, interstitial fluid) of mammals has been clearly demonstrated. Most of the extracellular phytate (in tissues, organs and biological fluids) comes from exogenous sources (mainly dietetic although it can also be applied topically or by other administration routes) and is not a consequence of endogenous synthesis. The physiological levels needed for the molecule to exercise its biological activity depend on exogenous administration, either oral, topical or via injection and in the form of a functional food, vitamin supplement or drug.

In this invention, an "inhibitor of dissolution" is understood to mean a substance that is capable of preventing or reducing the re-dissolution of already formed salts.

This composition can be administered by any known route, such as oral, parenteral, topical, subcutaneous, intravenous or intramuscular as the biological activity of phytate as an inhibitor of dissolution depends on exogenous sources.

It is well known by persons skilled in the art that the inhibitors of crystallisation, in this case phytate, exert their action by their capacity to adsorb on the surface of the crystal or crystalline nucleus in formation. The high negative electrical charge of phytate and the spatial disposition of its phosphate groups (phytate is the only inositol polyphosphate identified in eukaryotic cells that has the phosphate groups in positions 1, 2, 3 equatorial-axial-equatorial) give it much higher capacity to adsorb onto crystal surfaces than other compounds, particularly the other inositol phosphates with a smaller number of phosphate groups, such as inositol triphosphate disclosed in U.S. Pat. Nos. 5,057,507 and 5,015,634.

The apparently contradictory fact that phytate is one of the inhibitors of crystallisation of calcium salts (both as regards nucleation and crystal growth) and that it is also effective in preventing their dissolution can be clearly explained by considering the mechanism of formation and destruction of a crystal. Thus, as was previously indicated, the action of phytate as inhibitor of crystallisation is attributed to its capacity to adsorb on the surface of the crystal or crystalline nucleus in formation, preventing the arrival of new atoms of material, in this way preventing the crystal from growing or the crystalline nucleus from reaching its critical size. At the same time, the adsorption of the inhibitor on the critical points of the crystal surface contribute to its stabilisation, preventing the material of the crystal from passing into solution, in this way preventing the process of crystal destruction (dissolution). The inhibitor therefore acts in both directions, preventing the process of formation but also stabilising the already formed solid, preventing both its subsequent growth and its dissolution.

Phytate may be the only active principle of the composition utilised. However, other active pharmaceutical principles may also be present, or it may be presented in the form of functional foods, dietetic supplements, food supplements, vitamin supplements, nutritional supplements, or phytotherapeutic products because, as has been previously described, its bioavailability depends on exogenous supply.

In the manufacture of a phytate medicament, phytate may be used with a common pharmaceutically acceptable additive, an excipient or a vehicle.

EXAMPLES OF EMBODIMENTS OF THE PRESENT INVENTION

The present invention is illustrated by the following examples that do not limit its scope in any way.

Example 1

Three homogenous suspensions of crystallised calcium phosphate in the form of hydroxyapatite in TRIS buffer at pH 7.4 were prepared. These suspensions were stirred for 8 hours in the presence of 1, 3 and 12 uM of phytate, respectively. Later, the suspensions were filtered and the amount of phytate adsorbed on the hydroxyapatite crystals was determined by difference between the initial and final phytate in the solution at pH 7.4. The results obtained indicated that 62, 66 and 56%, respectively, of phytate present in the solution remained fixed to the calcium phosphate structure (hydroxyapatite), showing that phytate adsorbs strongly on calcium salts and can exercise actions related to this property.

Example 2

A homogenous suspension of crystalline calcium phosphate in the form of hydroxyapatite in TRIS buffer at pH 7.4 was prepared. This suspension was stirred for 8 hours. Then the crystals obtained were filtered and dried to constant weight. Then these crystals were resuspended at pH 5.0 (in acetate buffer) and the kinetics of dissolution of the salt was determined over 24 hours, continuously stirring the system. The kinetics were followed by determining the quantity of dissolved calcium and phosphorus by atomic emission spectroscopy (using inductively coupled plasma).

This experiment was repeated using concentrations of 1, 6 and 12 uM of phytate during the stage at pH 7.4 with the aim of fixing this compound on the hydroxyapatite structure.

The results obtained are shown in FIG. 1. They show that the phytate fixed on the calcium phosphate structure (hydroxyapatite) is capable of inhibiting the dissolution of the salt.

Example 3

A homogenous suspension of crystalline calcium phosphate in the form of hydroxyapatite in TRIS buffer at pH 7.4 was prepared. This suspension was stirred for 8 hours. Then the crystals obtained were filtered and dried to constant weight. Then these crystals were resuspended at pH 5.0 (in acetate buffer) and the kinetics of dissolution of the salt was determined over 24 hours, continuously stirring the system. The kinetics were followed by determining the quantity of dissolved calcium and phosphorus by atomic emission spectroscopy (using inductively coupled plasma).

This experiment was repeated using concentrations of 12 and 24 uM of phytate in the pH 5 stage with the aim of studying the inhibitory effect of dissolution by phytate present in the solution.

Figure 2:
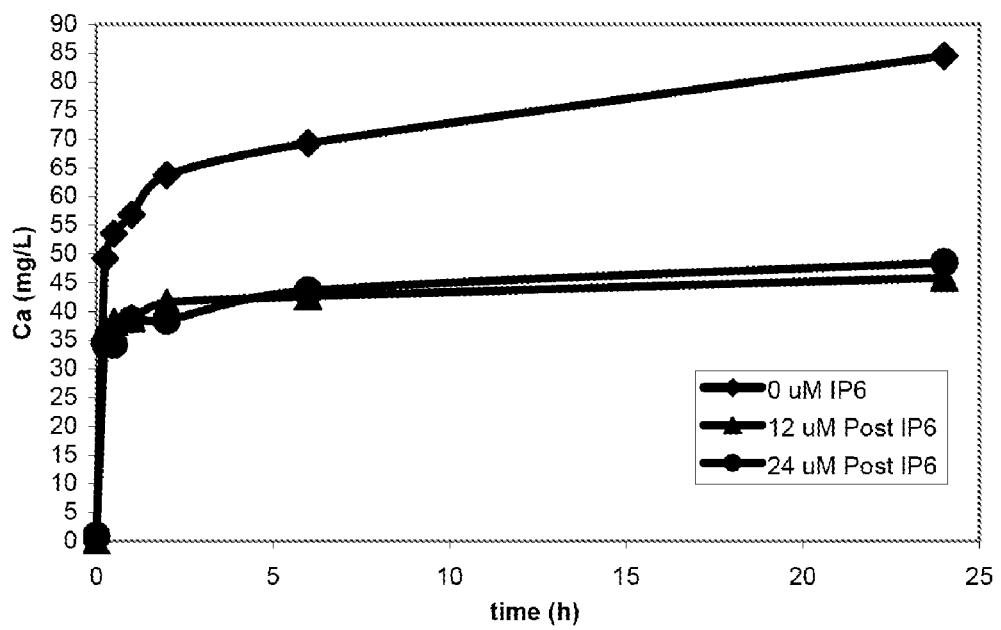
FIG. 2 is a graph showing the quantity of calcium dissolved on treating hydroxyapatite for a period of 24 hours in the presence of various concentrations of phytate at pH5.

The results obtained are shown in FIG. 2. They show that the phytate added at the stage of dissolution of hydroxyapatite (pH 5) is also capable of inhibiting the dissolution of the salt.

Example 4

A study was carried out evaluating the effect of phytate consumption on the level of bone mass measured by axial densitometry and peripheral heel densitometry. In total, 433 axial densitometer measurements and 1473 peripheral heel densitometer measurements were made. The consumption of phytate by all subjects was evaluated by using a dietetic questionnaire. Subjects were classified into 4 groups (group 1, group 2, group 3 and group 4) according to increasing levels of phytate consumption.
The results of the average T-score were as follows:
Spinal column: group 1 (−1.48 SD 1.255), group 2 (−0.876 SD 1.135)[a], group 3 (−0.557 SD 1.349)[a], group 4 (−0.428 SD 1.219)[a,b].
Femoral neck: group 1 (−0.774 SD 1.016), group 2 (−0.166 SD 51.109)[a], group 3 (−0.02 SD 1.188)[a], group 4 (0.168 SD 1.132)[a,b].
Heel bone: group 1 (−0.664 SD 1.092), group 2 (−0.1411 SD 1.077)[a], group 3 (0.3221 SD 1.167)[a,b], group 4 (0.3283 SD 1.242)[a,b].
[a]$p<0.05$ v group 1; [b]$p<0.05$ v group 2

These results indicate that the consumption of a diet rich in phytate results in higher bone mass. Therefore phytate has clear potential for the prevention and treatment of osteoporosis.

Example 5

Composition containing 120 mg phytine (calcium-magnesium phytate) and dietetic fibre as a vehicle.

Having demonstrated the positive influence of phytate on bone mass and knowing the relationship between the physiological phytate levels and its exogenous supply, this example composition (which can be used as a pharmaceutical composition or nutritional complement) may be used for prevention/treatment of osteoporosis.

Example 6

Adding cereals rich in phytate (calcium-magnesium salt) to a yogurt. Having demonstrated the positive influence of phytate on bone mass and knowing the relationship between the physiological phytate levels and its exogenous supply, this example functional food may be used for prevention/treatment of osteoporosis.

Example 7

Composition of a typical gel for topical application

| | |
|---|---|
| Water | 90% |
| Propylene glycol | 6% |
| PNC 400 | 2% |
| Sodium phytate | 2% |

Having demonstrated the positive influence of phytate on bone mass and knowing the relationship between the physiological phytate levels and its exogenous supply, this example composition for topical application may be used for prevention/treatment of osteoporosis.

The invention claimed is:
1. A method of inhibiting, delaying or treating osteoporosis, comprising administering to a subject in need thereof an effective amount of myo-inositol hexaphosphate of formula (I):

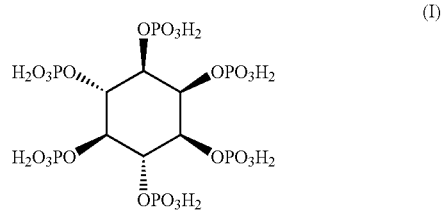

or a pharmaceutically acceptable salt thereof or mixture thereof.
2. The method of claim 1, wherein the myo-inositol hexaphosphate is administered in the form of a functional food.
3. The method of claim 1, wherein the myo-inositol hexaphosphate is administered in the form of a dietetic complement.
4. The method of claim 1, wherein the myo-inositol hexaphosphate is administered in the form of a vitamin complement.
5. The method of claim 1, wherein the myo-inositol hexaphosphate is administered in the form of a nutritional complement.

* * * * *